United States Patent [19]

Golman

[11] Patent Number: 4,650,671

[45] Date of Patent: Mar. 17, 1987

[54] ANTIPERSPIRANT KIT AND METHOD FOR CONTROLLING PERSPIRATION

[75] Inventor: Klaes Golman, Rungsted Kyst, Denmark

[73] Assignee: Claus Riemann & Co. ApS, Holte, Denmark

[21] Appl. No.: 605,762

[22] Filed: May 1, 1984

Related U.S. Application Data

[63] Continuation of Ser. No. 398,246, Jul. 14, 1982, abandoned.

[30] Foreign Application Priority Data

Jul. 17, 1981 [DK] Denmark ............................ 3221/81
Dec. 10, 1981 [DK] Denmark ............................ 5493/81

[51] Int. Cl.[4] .......................... A61K 7/34; A61K 7/38

[52] U.S. Cl. ........................................ 424/66; 424/47; 424/68

[58] Field of Search .................................... 424/66, 68

[56] References Cited

U.S. PATENT DOCUMENTS

| | | | |
|---|---|---|---|
| 2,230,084 | 1/1941 | Montenier | 424/65 X |
| 2,236,387 | 3/1941 | Wallace, Jr. et al. | 424/65 |
| 2,246,524 | 6/1941 | Kyrides | 424/65 X |
| 2,368,075 | 1/1945 | Wampner | 424/65 X |
| 2,498,514 | 2/1950 | Van Mater | 424/66 |
| 2,507,128 | 9/1950 | Wainer | 424/66 |
| 2,814,585 | 11/1957 | Daley | 424/66 |
| 3,745,033 | 7/1973 | Hutchison | 424/65 |
| 3,775,538 | 11/1973 | De Salva et al. | 424/65 |
| 3,959,459 | 5/1976 | Curry | 424/65 |

FOREIGN PATENT DOCUMENTS

| | | | |
|---|---|---|---|
| 0835385 | 5/1960 | United Kingdom | 424/66 |

*Primary Examiner*—Dale R. Ore
*Attorney, Agent, or Firm*—Stiefel, Gross, Kurland & Pavane

[57] ABSTRACT

Method for controlling perspiration, and kit for carrying out that method. The method involves the separate, sequential application of an $AlCl_3$— or $ZrCl_4$— containing antiperspirant composition and a physiologically tolerable basic buffer-containing composition. The kit involves separate applicators for applying the $AlCl_3$— or $ZrCl_4$— containing antiperspirant, and the buffer. Separate, successive application of the antiperspirant and the buffer prevents skin irritation or damage to the user's clothes attributable to acid formed from the antiperspirant, and provides antiperspirant activity which is equal or superior to previously known $AlCl_3$— or $ZrCl_4$— antiperspirants.

22 Claims, No Drawings

ANTIPERSPIRANT KIT AND METHOD FOR CONTROLLING PERSPIRATION

This is a continuation of application Ser. No. 398,246, filed July 14, 1982.

The present invention relates to an antiperspirant kit, an applicator with a composition which may be used in the kit, and a method for controlling perspiration without the disadvantages often associated with such methods.

It is a well-known fact that $AlCl_3$ is a most effective antiperspirant salt (Hølze E., Kligman A.: Mechanism of antiperspirant action of aluminium salts. J. Soc. Cosmet. Chem. 30, 279 (1979), and Shelley B., Hurley HJ.: Studies on topical antiperspirant control of axillary hyperhidrosis. Acta Dermatoven. (Stockh.) 55, 241, (1975)). Most of the commercially available antiperspirant compositions contain $AlCl_3$ as the active component, dissolved in a suitable solvent. The soluble form of $AlCl_3$ is $AlCl_3.6H_2O$; it will be understood that in the present specification and claims, whenever $AlCl_3$ solutions are discussed, the dissolved form is $AlCl_3.6H_2O$. Any solutions which are substantially non-aqueous have the desired effect. In the present context, the term "substantially nonaqueous" designates a solution which does not contain free water to such an extent that the $AlCl_3$ content thereof is decreased so much due to reaction with water with resulting formation of $Al(OH)_3$ and HCl that the antiperspirant activity of the solution has substantially decreased. Typically, the water content of effective antiperspirant $AlCl_3$ solutions will be less than 20% by volume, preferably less than 10% by volume. Normally, the $AlCl_3$ solution will be prepared using an anhydrous medium, and the water content of the solution will increase gradually as a result of the hygroscopicity of such solution. Typically, it will take several years before an $AlCl_3$ solution prepared in a non-aqueous medium and stored under normal storage conditions has absorbed water to such an extent that its antiperspirant activity has essentially decreased. The activity of $AlCl_3$ as an antiperspirant depends on the concentration of the $AlCl_3$ in the solution; saturated solutions of $AlCl_3$ represent the upper limit of activity. Only solutions which are substantially anhydrous have the desired effect. A 25% solution of $AlCl_3.6H_2O$ in anhydrous ethanol is acknowledged as being a superior topical agent for control of axillary sweat; the activity of this 25% solution has been confirmed in clinical studies.

The antiperspirant activity of the $AlCl_3$-containing anhydrous solution is believed to be due to the formation of a perspiration-blocking "cast" of an aluminum-containing polymeric gel precipitate in the sweat ducts when water having a pH in the neutral range reacts with the $AlCl_3$ in the sweat ducts.

However, such a solution of $AlCl_3.6H_2O$ has certain disadvantages. In particular, it may cause local skin irritation; in most clinical studies, 20–50 percent of the members of the test groups indicated that irritation occurred, and about 10 percent reported about severe irritation (soreness). Also, clothes in contact with the application area may be damaged. Both of these adverse effects are ascribable to the development of acid resulting from reaction between water (sweat) and $AlCl_3$ on the skin and in the sweat ducts. Furthermore, the acidity generated in sweat which reacts with $AlCl_3$ will severely impair the efficiency of the $AlCl_3$ solution as $AlCl_3$ is not capable of forming the above-mentioned gel precipitate when the water with which it reacts has a pH of less than 5; among other things, this means that the solution is not effective when used during sweating.

In the known art, several attempts have been made to overcome the development of acid which causes skin irritation and damaging of clothes, and several vehicles have been proposed for $AlCl_3$-containing antiperspirant compositions. Thus, e.g., it has been suggested to add buffers to the $AlCl_3$ solutions. However, these attempts have resulted in a decrease of the antiperspirant efficiency of $AlCl_3$, which must be presumed to be due to undesired premature neutralization thereof.

It has now been found that if an anhydrous fluid composition containing a physiologically tolerable basic buffer capable of neutralizing acid developed from the applied $AlCl_3$ is applied after the application of $AlCl_3$-containing antiperspirant composition, the skin-irritating and clothes-damaging acid formation may be suppressed, but the $AlCl_3$ will still be capable of reaching into the sweat ducts to form the essential polymeric gel cast therein before it is neutralized.

Hence, one aspect of the present invention relates to an antiperspirant kit comprising

- an applicator containing, and adapted for applying to the skin, a fluid $AlCl_3$-containing antiperspirant composition, and
- an applicator containing, and adapted for applying to the skin, an anhydrous fluid composition comprising a physiologically tolerable basic buffer capable of neutralizing acidic substances developed from the applied $AlCl_3$.

The buffer should have the following properties:

(1) it should be substantially non-aqueous, (2) $AlCl_3$ should be insoluble or only slightly soluble in the buffer, (3) as one mole of $AlCl_3$ is capable of generating three moles of HCl, the buffer should be capable of being applied on the skin in a considerable amount in order to be effective, which means that the buffer should either be readily soluble in a physiologically tolerable solvent (anhydrous), or it should be fluid at ambient temperature, (4) the buffer per se should be non-toxic, i.e. should have substantially no irritating effects on the tissue, and (5) the smell of the buffer should not be unpleasant.

Preferred basic buffers are amines, and preferred amines are amines with a molecular weight below about 1,000. Preferred amines are fluid at room temperature.

Amines usable according to the invention are amines of the general formula

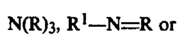

$N(R)_3$, $R^1—N=R$ or $$R—\overset{\displaystyle R^1}{\overset{|}{N}}—R^2$$

wherein each of R, $R^1$, and $R^2$ designates a hydrogen atom or a hydrocarbon group containing up to 10 carbon atoms and optionally oxygen and being selected from the group consisting of saturated or unsaturated, unbranched or branched alkyl or hydroxyalkyl groups, and saturated or unsaturated cyclic alkyl groups, said groups optionally containing one or two oxy groups and optionally being interrupted by 1 or 2 primary or secondary nitrogen atoms, with the proviso that at most two of R, $R^1$ and $R^2$ designate hydrogen.

Specific amines to be mentioned are amines selected from the group consisting of: $(CH_3CHOHCH(CH_3))_2NH$, $CH_3(CH_2)_3N(CH_2OH)_2$, $HOCH_2CH_2N(CH_2CHOHCH_2CH_3)_2$, $H_2NCH_2CH_2NHCH_2CH_2OH$, $CH_3N(CH_2CH_2OH)_2$, $(CH_3CH_2CH_2C(CH_3)OHCH_2)_2NH$, $CH_3N(CH_2CH_2CH_2CH_2OH)_2$, $N(CH_2CH_2OH)_3$, $HN(CH_2CH_2OH)_2$ and $H_2N(CH_2CH_2OH)$.

A particularly preferred amine is triethanolamine.

Triethanolamine may be applied per se or in solution.

In a preferred embodiment of the invention, the composition comprising the buffer is a solution of triethanolamine in a solvent which has no adverse influence on the antiperspirant.

As water contained in the solvent would react with $AlCl_3$ and thus decrease the antiperspirant activity, such as explained above, the solvent should be anhydrous.

Furthermore, the solvent should be a solvent in which the triethanolamine is readily soluble. A preferred solvent for the triethanolamine is anhydrous ethanol.

The triethanolamine may be present in the solution in a concentration of about 10–100 percent (calculated on the total amount) triethanolamine in the solvent. A preferred concentration range is 20–75 percent, and the most preferred range is 25–50 percent of triethanolamine. The most preferred buffer solution is a 25 -50 percent solution of triethanoalamine in anhydrous ethanol.

By applying an effective amount of a substantially anhydrous solution of a buffer in which $AlCl_3.6H_2O$ is insoluble, neutralization of the HCl developed is achieved, and the $AlCl_3$ will be capable of entering into the sweat ducts where the formation of the polymeric gel will take place. It is presumed that the buffer will even increase the activity of aluminum chloride by increasing the pH in the sweat duct.

A preferred antiperspirant kit according to the invention is a kit wherein the solution of the buffer is an about 25–50 percent solution of triethanolamine in anhydrous ethanol.

The $AlCl_3$-containing composition of the kit of the invention is preferably a solution of $AlCl_3.6H_2O$ in an anhydrous solvent, and a preferred solution is an about 25 percent solution of $AlCl_3.6H_2O$ in anhydrous ethanol.

The antiperspirant kit comprising the above-mentioned first and the second applicators is preferably used in the following manner:

(1) the solution of $AlCl_3$-containing composition is applied to the skin and left to dry (about 1 minute), and (2) the buffer solution is applied.

The applicators may be of any suitable type, e.g. aerosol applicators, brush applicators, or, preferably, "roll-on" ball applicators.

Another aspect of the invention relates to an applicator adapted for application of a fluid composition on the skin and containing, as a fluid composition, an anhydrous fluid composition comprising a physiologically tolerable basic buffer which shows the features discussed above. The applicator may be of any of the suitable types for the purpose, suitably one of the types discussed above, and the fluid composition will be one of the composition types discussed above.

A further aspect of the invention relates to a method for controlling perspiration, said method comprising applying to a skin area, where perspiration is to be controlled, an anhydrous fluid $AlCl_3$-containing antiperspirant composition, and subsequently an anhydrous fluid composition comprising a physiogloically tolerable basic buffer capable of neutralizing acid developed from the applied $AlCl_3$.

Also in this method the physiologically tolerable basic buffer, as well as the fluid composition containing the buffer, are of the types discussed above. In accordance with the above explanation, the composition containing the buffer is suitably applied as soon as the $AlCl_3$-containing composition has dried.

The principles of the present invention, as exemplified by the use of triethanolamine as the physiologically tolerable buffer give the following advantages:

(1) no skin irritation occurs as the HCl developed from $AlCl_3$ is neutralized, (2) no damaging of the clothes takes place, (3) the antiperspirant kit can be used at any time, provided that the skin is dry before the first application, and (4) as triethanolamine is rather viscous at 37° C. and therefore provides a kind of "coating" of $AlCl_3$ which tends to prevent $AlCl_3$ from being physically removed from the skin, such as might otherwise take place with known art $AlCl_3$ antiperspirant compositions.

In addition, as mentioned above, that the antiperspirant activity may be achieved more readily and within a shorter time as the rate of neutralization increases.

Furthermore, in contrast to known art $AlCl_3$-containing antiperspirant compositions, the antiperspirant combinations of the present invention are not to the same extent limited to application in the evening or other times when the axillary skin is dry; the neutralizng effect of the buffer renders it possible to utilize the antiperspirant effect of the $AlCl_3$ under a broader range of conditions.

In the literature (Shelley B, Hurley HJ: Studies on topical antiperspirant control of axillary hyperhidrosis. Acta Dermatoven. (Stockh.) 55, 241, (1975)), it has been recorded that $ZrCl_4$ has similar antiperspirant activity as $AlCl_3$ according to a similar mechanism. For this reason, it is contemplated, according to the present invention, that the same problems with respect to generation of acidity due to reaction with water as discussed above for $AlCl_3$, and the solution of these problems according to the principles of the present invention, would also apply to $ZrCl_4$ and antiperspirant compositions concerning $ZrCl_4$. Therefore, it will be understood that whenever the present specification mentions $AlCl_3$, a similar teaching is also relevant to $ZrCl_4$, and the particular measures which are taken in connection with $AlCl_3$-containing compositions are also, according to this aspect of the invention, taken in connection with $ZrCl_4$-containing solutions.

The following example illustrates the invention

EXAMPLE (1) 25 g of $AlCl_3.6H_2O$ were dissolved in 100 g of absolute ethanol and filled into a common antiperspirant "roll-on" ball applicator.

(2) 50 ml of triethanolamine were dissolved in 50 ml of absolute ethanol and filled into a common antiperspirant "roll-on" applicator.

Colouring and perfumes may be added to either of the solutions, provided the pH in the solution is not substantially affected.

This antiperspirant kit was tested by ten volunteers, all of whom confirmed that no skin irritation and no damaging of clothes occurred when the composition comprising the triethanolamine was used after the application of the $AlCl_3$-containing composition, and that excellent antiperspirant effect was obtained.

I claim:

1. An antiperspirant kit comprising:

(1) an applicator containing, and adapted to apply to the skin, a substantially anhydrous liquid $AlCl_3$ or $ZrCl_4$-containing antiperspirant composition, and (2) an applicator containing, and adapted to apply to the skin, a substantially anhydrous liquid buffer composition comprising a physiologically tolerable basic buffer for neutralizing acids developed from the applied $AlCl_3$ or $ZrCl_4$, the $AlCl_3$ or $ZrCl_4$ being insoluble or only slightly soluble in the buffer and the buffer being substantially non-aqueous and readily soluble in a physiologically tolerable anhydrous solvent in said buffer composition.

2. An antiperspirant kit according to claim 1 wherein the $AlCl_3$-containing solution is a 10–25% solution of $AlCl_3.6H_2O$ in anhydrous ethanol.

3. An antiperspirant kit according to claim 1 wherein the basic buffer is an amine having a molecular weight below about 1000.

4. An antiperspirant kit according to claim 3 wherein the amine has the general formula $N(R)_3$, $R_1—N{=}R$ or

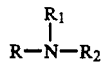

each of R, $R^1$ and $R^2$ being a member selected from the group consisting of hydrogen, and alkyl, cyclic alkyl, and hydroxyalkyl groups containing up to ten carbon atoms, said groups containing up to two oxy groups and up to two primary and secondary nitrogen atoms, and at most two of R, $R_1$ and $R_2$ being hydrogen.

5. An antiperspirant kit according to claim 4 wherein the amine is selected from the group consisting of: $(CH_3CHOHCH(CH_3))_2NH$, $CH_3(CH_2)_3N(CH_2OH)_2$, $HOCH_2CH_2N(CH_2CHOHCH_2CH_3)_2$, $H_2NCH_2CH_2NHCH_2CH_2OH$, $CH_3N(CH_2CH_2OH)_2$, $(CH_3CH_2CH_2C(CH_3)OHCH_2)_2NH$, $CH_3N(CH_2CH_2CH_2OH)_2$, $N(CH_2CH_2OH)_3$, $HN(CH_2CH_2OH)_2$ and $H_2N(CH_2CH_2OH)$.

6. An antiperspirant kit according to claim 4 wherein the amine is triethanolamine.

7. An antiperspirant kit according to claim 6 wherein the buffer composition is a 20–75 percent solution of triethanolamine in anhydrous ethanol.

8. An antiperspirant kit according to claim 6 wherein the composition comprising the buffer is a solution of triethanolamine in an anhydrous solvent.

9. An antiperspirant kit for carrying out the method of claim 23, which comprises (1) an applicator containing, and adapted to apply to the skin, a substantially anhydrous liquid $AlCl_3$ or $ZrCl_4$-containing antiperspirant composition, and (2) an applicator containing, and adapted to apply to the skin, a substantially anhydrous liquid buffer composition comprising a physiologically tolerable basic buffer for neutralizing acids developed from the applied $AlCl_3$ or $ZrCl_4$, the $AlCl_3$ or $ZrCl_4$ being insoluble or only slightly soluble in the buffer and the buffer being substantially non-aqueous and readily soluble in a physiologically tolerable anhydrous solvent in said buffer composition.

10. An antiperspirant kit according to claim 9, wherein the basic buffer is an amine having a molecular weight below about 1000.

11. An antiperspirant kit according to claim 10, wherein the amine has the general formula $N(R)_3$, $R_1—N{=}R$ or each of R, $R^1$ and $R^2$ being a member selected from the group consisting of hydrogen, and alkyl, cyclic alkyl, and hydroxyalkyl groups containing up to ten carbon atoms, said groups containing up to two oxy groups and up to two primary and secondary nitrogen atoms, and at most two of R, $R_1$ and $R_2$ being hydrogen.

12. An antiperspirant kit according to claim 11, wherein the amine is selected from the group consisting of: $(CH_3CHOHCH(CH_3))_2NH$, $CH_3(CH_2)_3N(CH_2OH)_2$, $HOCH_2CH_2N(CH_2CHOHCH_2CH_3)_2$, $H_2NCH_2CH_2CH_2NHCH_2CH_2OH$, $CH_3N(CH_2CH_2OH)_2$, $(CH_3CH_2CH_2C(CH_3)OHCH_2)_2NH$, $CH_3N(CH_2CH_2CH_2OH)_2$, $N(CH_2CH_2OH)_3$, $HN(CH_2CH_2OH)_2$ and $H_2N(CH_2CH_2OH)$.

13. An antiperspirant kit according to claim 11, wherein the amine is triethanolamine.

14. An antiperspirant kit according to claim 13, wherein the buffer composition is a 20–75 percent solution of triethanolamine in anhydrous ethanol.

15. An antiperspirant kit according to claim 9, wherein the antiperspirant composition solution is a 10–25 percent solution of $AlCl_3.6H_2O$ in anhydrous ethanol.

16. A method for controlling perspiration, comprising applying, to a skin area where perspiration is to be controlled:

(a) a substantially anhydrous liquid $AlCl_3$- or $ZrCl_4$-containing antiperspirant composition, and subsequently (b) a substantially anhydrous liquid buffer composition comprising a physiologically tolerable basic buffer for neutralizing acids developed from the applied $AlCl_3$ or $ZrCl_4$, the $AlCl_3$ or $ZrCl_4$ being insoluble or only slightly soluble in the buffer and the buffer being substantially non-aqueous and readily soluble in a physiologically tolerable anhydrous solvent in said buffer composition.

17. A method according to claim 16 wherein the basic buffer is an amine having a molecular weight below about 1000.

18. A method according to claim 16 wherein the buffer composition is triethanolamine in anhydrous ethanol.

19. A method according to claim 16 wherein the amine is selected from the group consisting of: $(CH_3CHOHCH(CH_3))_2NH$, $CH_3(CH_2)_3N(CH_2OH)_2$, $HOCH_2CH_2N(CH_2CHOHCH_2CH_3)_2$, $H_2NCH_2CH_2NHCH_2CH_2OH$, $CH_3N(CH_2CH_2OH)_2$, $(CH_3CH_2CH_2C(CH_3)OHCH_2)_2NH$, $CH_3N(CH_2CH_2CH_2OH)_2$, $N(CH_2CH_2OH)_3$, $HN(CH_2CH_2OH)_2$ and $H_2N(CH_2CH_2OH)$.

20. A method according to claim 17 wherein the amine has the general formula $N(R)_3$, $R_1—N=R$ or

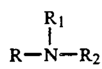

each of R, $R^1$ and $R^2$ being a member selected from the group consisting of hydrogen, and alkyl, cyclic alkyl, and hydroxyalkyl groups containing up to ten carbon atoms, said groups containing up to two oxy groups and up to two primary and secondary nitrogen atoms, and at most two of R, $R_1$ and $R_2$ being hydrogen.

21. A method according to claim 20 wherein the amine is triethanolamine.

22. A method according to claim 16 wherein the composition comprising the buffer is a solution of triethanolamine in an anhydrous solvent.

* * * * *

UNITED STATES PATENT AND TRADEMARK OFFICE

CERTIFICATE OF CORRECTION

PATENT NO. : 4,650,671

DATED : March 17, 1987

INVENTOR(S) : Klaes Golman

It is certified that error appears in the above-identified patent and that said Letters Patent is hereby corrected as shown below:

Column 1, line 26 = "nonaqueous" should read --non-aqueous--

Column 3, line 29 = "25 -50" should read --25-50--

Column 3, line 30 = "triethanoalamine" should read --triethanolamine--

Column 4, lines 5,6 = "physiogloically" should read --physiologically--

Column 4, line 24 = "37°C." should read --37°C--

Column 4, line 37 = "neutralizng" should read --neutralizing--

Column 4, line 60 = after "invention" insert a colon--:--

Column 5, line 62 = "claim 23" should read --claim 16--

Column 6, line 12 = after "R1-N=R or "insert

UNITED STATES PATENT AND TRADEMARK OFFICE

CERTIFICATE OF CORRECTION

PATENT NO. : 4,650,671

DATED : March 17, 1987

INVENTOR(S) : Klaes Golman

It is certified that error appears in the above-identified patent and that said Letters Patent is hereby corrected as shown below:

Column 6, line 12 = after "R1-N=R or "insert --

$$--R-N(R^1)-R^2--$$

Signed and Sealed this

Twenty-second Day of September, 1987

*Attest:*

DONALD J. QUIGG

*Attesting Officer* *Commissioner of Patents and Trademarks*